United States Patent
Sapia et al.

[11] Patent Number: 5,089,700
[45] Date of Patent: Feb. 18, 1992

[54] APPARATUS FOR INFRARED IMAGING INSPECTIONS

[75] Inventors: Mark A. Sapia, Canton; John G. Clark, Enfield, both of Conn.

[73] Assignee: Amdata, Inc., Windsor, Conn.

[21] Appl. No.: 472,512

[22] Filed: Jan. 30, 1990

[51] Int. Cl.$^5$ .............................................. G01J 5/20
[52] U.S. Cl. .................................... 250/330; 250/340; 250/342
[58] Field of Search .............. 250/330, 340, 342, 334, 250/336.1

[56] References Cited

U.S. PATENT DOCUMENTS 3,868,508  2/1975  Lloyd .................................... 250/330

FOREIGN PATENT DOCUMENTS 2174803  11/1986  United Kingdom ................ 250/342

OTHER PUBLICATIONS

"Barnes Infrared Camera", Defense & Space Division, Barnes Engineering Company, 1963, pp. 1-12.
Sunshine et al., "Direct Observation of the Effect of Solder Voids on the Current Uniformity of Power Transistors", IEEE Transactions on Electron Devices, 1975, pp. 61-62.
Weight et al., "Thermography Testing of Production P.C. Boards", Electronic Packaging & Production, 1981, pp. 69-73.
White et al., "Observation of Carrier Densities in Silicon Devices by Infrared Emissions", J. Phys: E. Sci. Instru., vol. 10, pp. 817-825, 1977.

Primary Examiner—Constantine Hannaher
Assistant Examiner—Edward J. Glick
Attorney, Agent, or Firm—John H. Mulholland

[57] ABSTRACT

A method of nondestructively identifying regions "R" of high density in a substrate (10) of a bonded matrix of carbon fibers by resistively heating the substrate and taking an infrared image of the heated substrate. Terminals 12, 14, 16 and 18 are connected to a power supply 26 by wires 22 and cable 24 of which they are a part, to effect the heating.

9 Claims, 1 Drawing Sheet

APPARATUS FOR INFRARED IMAGING INSPECTIONS

BACKGROUND OF THE INVENTION

Fuel cells electrodes and other articles, which are basically matrices of carbon fiber and a binder such as phenolic resin, for a variety of reasons, desirably are of uniform density. In the particular case of fuel cell electrodes, if the fabrication process results in regions of the substrate being too high in density, it is a problem. More particularly, at the completion of the processing, when the electrode substrate is placed in service, overly dense regions may restrict the diffusion of oxygen or hydrogen gas. Thus, the performance of the fuel cell may be impaired.

In the case of aircraft structural part substrates, such as airframe parts, uniformity of density is desirable because it translates into uniformity of strength per unit measure of material.

Currently, there is no easily applied method to nondestructively test resin bonded carbon fiber substrates such as fuel cell electrodes except to visually inspect them. Upon examination, small areas can be tested. However, the present invention solves a particular problem in infrared imaging by creating a steady state temperature gradient around areas of high density. Other methods of heating produce temperature gradients in a transient state making it very difficult to capture and record an infrared image for analysis. More generally, the present invention improves the diagnostic value of infrared imaging of carbon composites over that of eddy current testing and ultrasonic testing.

SUMMARY OF THE INVENTION

The importance of the novel combination of procedural steps is the method of heating. It takes advantage of the fact that carbon is conductive yet resistive enough for I2R heating which solves the problem of the part, if otherwise heated, becoming uniformly heated over the entire area. Visual inspections previously required primarily a subjective decision whether to accept or reject a carbon composite part. The need for a non-destructive test method to quickly and quantitatively identify regions of high density or each of homogeneity has led to applying thermal imaging in the past. However, the results have been unsuccessful. The reason for this seems to be because some form of contact or convection heating has been relied upon to heat the electrodes for subsequent infrared (IR) imaging. The poor results occur because the fuel cell electrode being tested, for example, reaches thermal equilibrium (i.e., constant temperature throughout). There is but a short window of time to capture an image that shows temperature gradients formed due to regions of high and low density. Moreover, this time window may vary for different areas of the same part.

In contrast, the instant invention, because of the resistive heating, reverses the problem of reaching steady state thermal equilibrium. By electrically heating a fuel cell electrode, for example, the regions of high and low density correspond to regions of high and low conductivity. Similarly, if regions of non-homogeneity, voids, pitting or cracks are present in a substrate, they will show as regions of steady state thermal gradients. As current is passed through the electrode, current density increases in regions of high density and results in greater resistive heating. With this method, temperature gradients exist in steady state instead of in the transient response. The infrared images in this situation clearly distinguish regions of high and low density. When photographed or scanned with infrared ray emission imaging equipment attached to a video recording machine, pictures or tapes showing contrasting areas of temperature gradients which clearly distinguish regions of high and low density are provided.

DETAILED DESCRIPTION OF THE INVENTION

Figure 1:
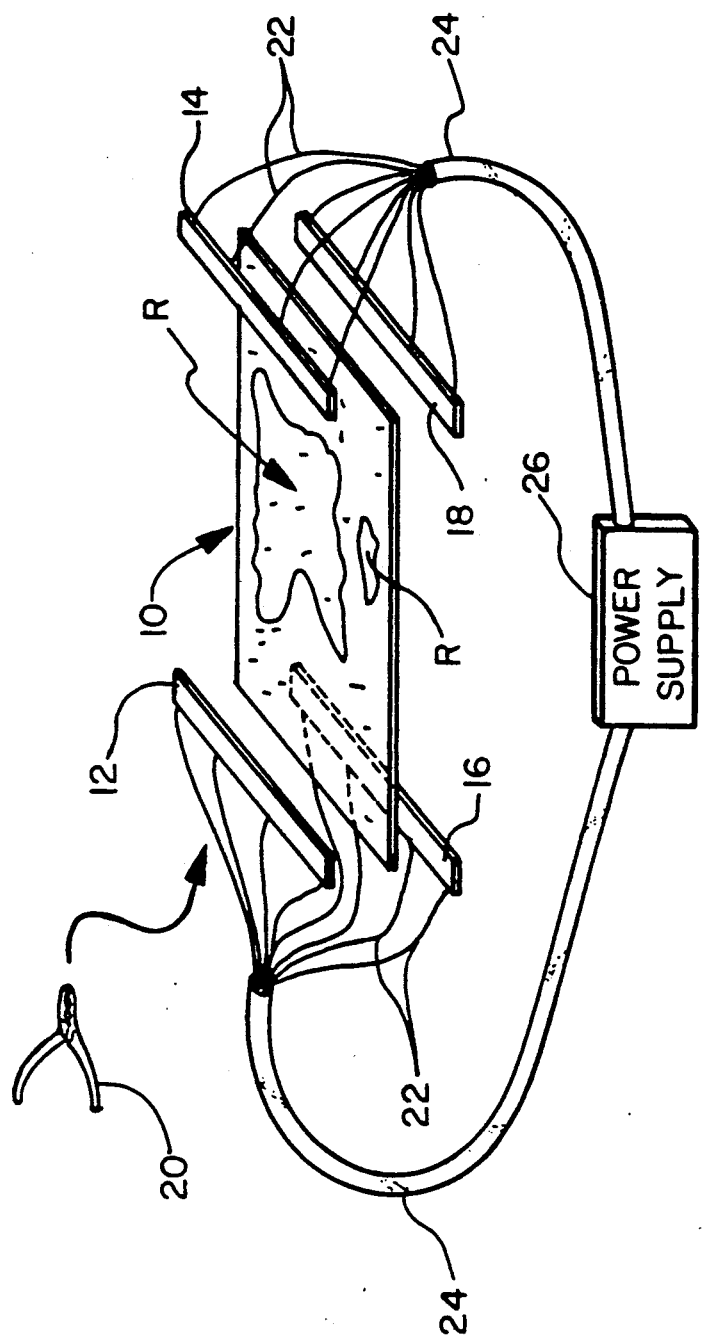
FIG. 1 is a schematic exploded view of a fuel cell electrode substrate of phenolic resin bonded carbon fibers showing the mode of application of alternating current from one substrate area extremity to the other in performing the method of nondestructively identifying regions of high density in the substrate area and recording them by photographing or scanning the area with infrared ray emission imaging equipment.

The method of nondestructively identifying high density regions "R" of a fuel cell electrode 10 made of phenolic resin bonded carbon fibers includes a procedural combination of steps of no critical sequence except that the photographing or scanning with imaging equipment follows a step of resistance heating to create contrasting areas of temperature gradients.

Typically, the method is performed by connecting copper or aluminum terminals or bars 12, 14, 16 and 18 at opposite extremities of and on opposite sides of the electrode 10. The bars 12 and 16 on opposite sides from each other on one end and the bars 14 and 18 on opposite sides from each other on the opposite end. The bars 12 and 16 are held at their end of the electrode substrate area by means of a plurality of clamps 20. In similar manner, the bars 14 and 18 are held at the opposite end of the electrode substrate area 10 to be imaged.

The bars 12, 14, 16 and 18 have attached thereto, wires 22 which are part of conductor cable 24 such that a substantially even current density is distributed within the bars 12, 14, 16 and 18. The cables 24 are suitably connected to a power supply 26.

By means of this arrangement, a current is applied through terminals and across the area of substrate 10, thereby to resistively heat and to create contrasting high density regions "R" of temperature gradients which clearly distinguish from the regions of the rest of the area of electrode 10 which is, relative to regions "R", of low density.

The electrodes 10 in their as-fabricated state typically can be heated by applying approximately 230 volts of alternating current (AC) across the substrate area. Once the electrodes are carbonized, the conductivity becomes very high. The electrodes 10 can still be tested using this method, however a power supply 26 capable of high current (120 amps or 3 amps per inch) is needed.

The electrodes 10, after electrical heating, as described, is photographed by a camera using infrared ray emission sensitive film or is scanned. The scanning can be performed with a Model 525 hand held or tripod mounted electronic imaging apparatus obtained from "INFRAMETRICS" of Billerica, Massachusetts 01862, which for certain high resolution shots can be supplemented with a 0.8 micron infrared filter from the same source. The Model 525 electronics pack attaches to a commercial VCR video cassette recorder to create magnetic recording tapes of the images produced from the scan.

The electrode 10 may be heated at any stage in the processing so that it can be thermally imaged to identify regions of high density.

I claim:

1. A method of nondestructively identifying regions of high density in a substrate of a bonded matrix of carbon fibers comprising the procedural combination of steps of:

connecting conductor terminals at opposite extremities of an area of a substrate of a bonded matrix of carbon fibers to be imaged;

connecting the conductor terminals to an electrical power supply to apply a current through the terminals and across the area of the substrate, thereby to heat and to create contrasting regions of temperature gradients which clearly distinguish regions of high and low density;

identifying and recording the regions of high and low density by photographing or scanning the area with infrared ray emission imaging equipment.

2. The method of claim 1 in which the conductor terminals are copper or aluminum bars and the step of clamping them to the substrate is included.

3. The method of claim 1 in which the step of connecting the conductor bars to the electrical power supply by means of cables is included.

4. The method of claim 1 in which the bonded matrix of carbon fibers are bonded by resin to make the substrate.

5. The method of claim 1 in which the electrical power supplied is alternating current.

6. The method of claim 5 in which the alternating current is applied approximately 230 volts.

7. The method of claim 5 in which the power supply provides the relatively high current of approximately 120 amps.

8. The method of claim 8 in which the recording is video recording.

9. A method of nondestructively identifying regions of irregular structure in a substrate of a bonded matrix of carbon by performing the steps of resistively heating the substrate and taking an infrared image of the heated substrate.

* * * * *